(12) United States Patent
Sadoff et al.

(10) Patent No.: US 8,771,709 B2
(45) Date of Patent: Jul. 8, 2014

(54) THERAPEUTIC VACCINATION AGAINST ACTIVE TUBERCULOSIS

(75) Inventors: Jerald Sadoff, Amsterdam (NL); Anisah Alyahya, Leiden (NL)

(73) Assignee: Crucell Holland B.V., Leiden (NL)

( * ) Notice: Subject to any disclaimer, the term of this patent is extended or adjusted under 35 U.S.C. 154(b) by 0 days.

(21) Appl. No.: 13/822,593

(22) PCT Filed: Sep. 19, 2011

(86) PCT No.: PCT/EP2011/066183
§ 371 (c)(1),
(2), (4) Date: Mar. 12, 2013

(87) PCT Pub. No.: WO2012/038367
PCT Pub. Date: Mar. 29, 2012

(65) Prior Publication Data
US 2013/0171193 A1    Jul. 4, 2013

Related U.S. Application Data

(60) Provisional application No. 61/403,751, filed on Sep. 20, 2010.

(30) Foreign Application Priority Data

Sep. 20, 2010   (EP) ..................... 10177667

(51) Int. Cl.
*A61K 39/04* (2006.01)
*A61K 49/00* (2006.01)
*A61K 39/12* (2006.01)

(52) U.S. Cl.
USPC ....... 424/248.1; 424/9.1; 424/9.2; 424/234.1; 536/23.1; 536/23.2

(58) Field of Classification Search
CPC ....... A61K 39/00; A61K 39/04; A61K 39/12; A61K 39/235; A61K 49/00; A01N 63/00
USPC ............... 424/9.1, 9.2, 23.1, 248.1; 536/23.1, 536/23.2
See application file for complete search history.

(56) References Cited

U.S. PATENT DOCUMENTS

| | | | |
|---|---|---|---|
| 5,057,540 A | 10/1991 | Kensil et al. |
| 5,122,458 A | 6/1992 | Post et al. |
| 5,385,839 A | 1/1995 | Stinski |
| 5,559,099 A | 9/1996 | Wickham et al. |
| 5,837,511 A | 11/1998 | Falck et al. |
| 5,837,520 A | 11/1998 | Shabram et al. |
| 5,846,782 A | 12/1998 | Wickham et al. |
| 5,851,806 A | 12/1998 | Kovesdi et al. |
| 5,965,541 A | 10/1999 | Wickham et al. |
| 5,981,225 A | 11/1999 | Kochanek et al. |
| 5,994,106 A | 11/1999 | Kovesdi et al. |
| 5,994,128 A | 11/1999 | Fallaux et al. |
| 6,020,191 A | 2/2000 | Scaria et al. |
| 6,040,174 A | 3/2000 | Imler et al. |
| 6,083,716 A | 7/2000 | Wilson et al. |
| 6,113,913 A | 9/2000 | Brough et al. |
| 6,225,289 B1 | 5/2001 | Kovesdi et al. |
| 6,261,823 B1 | 7/2001 | Tang et al. |
| 2004/0057963 A1 | 3/2004 | Andersen et al. |
| 2009/0123438 A1 | 5/2009 | Havenga et al. |

FOREIGN PATENT DOCUMENTS

| | | |
|---|---|---|
| EP | 0853660 B1 | 7/1997 |
| OA | 2004062607 A2 | 7/2004 |
| WO | 9003184 A1 | 4/1990 |
| WO | 9014837 A1 | 12/1990 |
| WO | 9611711 A1 | 4/1996 |
| WO | 9626281 A1 | 8/1996 |
| WO | 9822588 A2 | 5/1998 |
| WO | 9912568 A1 | 3/1999 |
| WO | 9941416 A2 | 8/1999 |
| WO | 0003029 A2 | 1/2000 |
| WO | 0029024 A1 | 5/2000 |
| WO | 0032754 A1 | 6/2000 |
| WO | 0029024 A9 | 11/2000 |
| WO | 0070071 A1 | 11/2000 |
| WO | 0166137 A1 | 9/2001 |
| WO | 0240665 A2 | 5/2002 |
| WO | 03000851 A2 | 1/2003 |
| WO | 0349763 A1 | 6/2003 |
| WO | 03046124 A2 | 6/2003 |
| WO | 03061708 A1 | 7/2003 |
| WO | 03078592 A2 | 9/2003 |
| WO | 2004001032 A2 | 12/2003 |
| WO | 2004004762 A1 | 1/2004 |
| WO | 2004020971 A2 | 3/2004 |
| WO | 2004037294 A2 | 5/2004 |

(Continued)

OTHER PUBLICATIONS

Radosevic, K., et al. Infections and Immunity, vol. 75, No. 8, pp. 4105-4115, 2007.*
Havenga, M., et al. Journal of General Virology, vol. 87, pp. 2135-2143, 2006.*
Ly, L.H., et al. Expert Reviews Vaccines, vol. 7, No. 5, pp. 635-650, 2008.*
Ha, S.-J., et al. Gene Therapy vol. 12, pp. 634-638, 2005.*

(Continued)

*Primary Examiner* — Rodney P Swartz
(74) *Attorney, Agent, or Firm* — TraskBritt, P.C.

(57) ABSTRACT

The invention provides a method for therapeutic treatment of a patient having active tuberculosis (TB), the method comprising: administering to the patient a recombinant adenovirus vector that comprises nucleic acid encoding the Ag85A, Ag85B and TB10.4 antigens of *Mycobactium tuberculosis* (Mtb). Advantageously, the method can be used to shorten conventional drug therapy for treating active TB.

10 Claims, 6 Drawing Sheets

(56) References Cited

FOREIGN PATENT DOCUMENTS

| WO | 2004083418 | A1 | 9/2004 |
|---|---|---|---|
| WO | 2005002620 | A1 | 1/2005 |
| WO | 2005080556 | A2 | 9/2005 |
| WO | 2006053871 | A2 | 5/2006 |
| WO | 2006108707 | A1 | 10/2006 |
| WO | 2007110409 | A1 | 10/2007 |
| WO | 2009117134 | A2 | 9/2009 |
| WO | 2010060719 | A1 | 6/2010 |
| WO | WO 2012/038367 | A1 | 3/2012 |

OTHER PUBLICATIONS

Caccamo, et al., Analysis of *Mycobacterium tuberculosis*—specific CD8 T-cells in patients with active tuberculosis and in individuals with latent infection, XP-002621785, PLos ONE www.plosone.org, May 2009, pp. 1-10, vol. 4, Issue 5, e5528.

Derrick, et al., The safety of post-exposure vaccination of mice infected with *Mycobacterium tuberculosis*, Laboratory of Mycobacterial Diseases and Cellular Immunology, Center for Biologies Evaluation and Research, Vaccine 26, 2008, pp. 6092-6098.

Ha et al., Therapeutic effect DNA vaccines combines with chemotherapy in a latent infection model after aerosol infection of mice with *Mycobacterium tuberculosis*, XP-002621337, Gene Therapy, www.nature.com/gt, 2003, pp. 1592-1599, vol. 10.

Ha et al., Protective effect on DNA vaccine during chemotherapy on reactivation and reinfection of *Mycobacterium tuberculosis*, XP-002621338, Gene Therapy, www.nature.com/gt, 2005, pp. 634-638, vol. 12.

Leyten et al., Human T-cell responses to 25 novel antigens encoded by genes of the dormacy regulon of *Mycobacterium tuberculosis*, ScienceDirect, www.sciencedirect.com. Microbes and Infection, 2006, pp. 2052-2060, vol. 8.

Okada et al., Novel prophylactic and therepeutic vaccine against tuberculosis, Vaccine, www.elsevier.com/locate/vaccine, 2009, pp. 3267-3270, vol. 27.

Radosevic, et al., Protective Immune Response to a Recombinant Adenovirus Type 35 Tuberculosis Vaccine in Two Mouse Strains: CD4 and CD8 T-Cell Epitope Mapping and Role of Gamma Interferon, Infection and Immunity, American Society for Microbiology, Aug. 2007, pp. 4105-4115, vol. 75, No. 8.

Romano et al., DNA vaccines against mycobacterial diseases, XP009144166, Expert Review Vaccines, Sep. 2009, pp. 1237-1250, vol. 8, No. 9.

Rook et al., Immunotherapeutics for tuberculosis in experimental animals: Is there a common pathway activated by effective protocols?, XP-002621335, Perspective, Jul. 15, pp. 191-198, vol. 196.

Silva et al., Immunotherapy with plasmid DNA encoding mycobacterial hsp65 in association with chemotherapy is more rapid and efficient form of treatment for tuberculosis in mice, Gene Therapy, dated 2005, pp. 281-287, vol. 12.

Thanh Hoang et al., Distinct Differences in the Expansion and Phenotype of TB10.4 Specific CD8 and CD4 T Cells after Infection with *Mycobacterium tuberculosis*, PLoS|One, Department of Infectious Disease Immunology, dated Jun. 2009, pp. 1-9, vol. 4, Issue 6.

Takatsu et al., WS-061 Immunity to mycobacterial infection, 14th ICI Abstract book, 14th International Congress of Immunology, XP-002664530, dated 2010.

Young et al., Expanded Polyfunctional T Cell Response to Mycobacterial Antigens in TB Disease and Contraction Post-Treatment, PLoS|One, XP-002621784, dated Jun. 2010, pp. 1-7, vol. 5, Issue 6, e11237.

Zhang et al., New drug candidates and therapeutic targets for tuberculosis therapy, Department of Molecule Microbiology & Immunology, dated Jan. 2006, pp. 21-27, vol. 11, No. ½.

Zhu et al., Therapeutic effects of Ag85B and MPT64 DNA vaccines in a murine model *Mycobacterium tuberculosis* infection, Vaccine, dated Aug. 31, 2005, pp. 4619-4624, vol. 23, Issue 37.

International Preliminary Report on Patentability Chapter II (IPEA/409), PCT/EP2011/066183, dated Sep. 14, 2012.

PCT International Search Report, PCT/EP2011/066183, dated Sep. 9, 2011.

\* cited by examiner

US 8,771,709 B2
THERAPEUTIC VACCINATION AGAINST ACTIVE TUBERCULOSIS

CROSS-REFERENCE TO RELATED APPLICATIONS

This application is a national phase entry under 35 U.S.C. §371 of International Patent Application PCT/EP2011/066183, filed Sep. 19, 2011, designating the United States of America and published in English as International Patent Publication WO 2012/038367 A1 on Mar. 29, 2012, which claims the benefit under Article 8 of the Patent Cooperation Treaty and under 35 U.S.C. §119(e) to U.S. Provisional Patent Application Ser. No. 61/403,751, filed Sep. 20, 2010, and under Article 8 of the Patent Cooperation Treaty to European Patent Application Serial No. 10177667.2, filed Sep. 20, 2010.

TECHNICAL FIELD

The disclosure relates to the field of biotechnology and health care. More particularly, it concerns novel methods for therapeutic vaccination of subjects having active tuberculosis.

BACKGROUND

Tuberculosis (TB) is a disease caused by infection with the slow-growing bacteria *Mycobacterium tuberculosis* (Mtb). TB can be either latent or active, the latter meaning that the bacteria are growing and causing symptoms. Most often, the bacteria are found in the lungs, which is called pulmonary TB, and which is contagious. Approximately a third of the world population is infected with Mtb and 5-10% of these individuals will develop active TB in the course of their lives. TB is responsible for more than two million deaths each year, with more than 90% of cases occurring in developing countries.

Current treatment of drug-susceptible TB typically consists of a cocktail of antibiotic drugs taken over a period of six months to one year or more for antibiotic-resistant strains as recommended by the World Health Organization (WHO). Even though a large proportion of actively replicating bacilli are killed within the first month of therapy, the remaining duration of treatment is required for the killing of slow-growing persisting Mtb bacteria that are primarily located inside cells, in order to prevent relapse of the disease. Discontinuation of therapy earlier than the six-month duration recommended by the WHO will result in relapse of disease due to the multiplication of the remaining bacteria, whereas strict adherence to the six-month therapy can result in cure rates of only over 90% under optimal circumstances.

However, there are several disadvantages of such lengthy treatment regimes. Indeed, the actual cure rate in many developing countries are below the 85% target cure rate set by the WHO, at times dipping below 50%. The low treatment success rate is attributed to poor patient compliance resulting in relapses in the form of multidrug and extremely drug-resistant TB (MDR-TB/XDR-TB). Therefore, adhering to all doses of the antibiotics is very important, and daily visits with a health professional observing the intake of the medicine(s) are involved to ensure patient compliance. This is known as directly observed therapy (DOT), which entails a high cost and logistical burden.

Despite the success of TB drug therapy in saving the lives of many since it was first introduced, the emergence of MDR and XDR-TB highlights the inherent limitations in the usage of antibiotics against bacteria.

Thus, there is still an urgent need for improved therapy against active TB in order to curb the current global TB epidemic.

One way of shortening the duration of the treatment of TB has been described in WO 2004/062607, and includes the use of weak acids or their precursors for the treatment of TB.

An alternative and independent route to fight TB is by vaccination. However, this approach generally aims at preventing TB, by inducing immune responses in people that do not have active TB (and preferably are not even infected with Mtb when vaccinated), and thus the vaccines in this approach are prophylactic vaccines. Bacille Calmette-Guérin (BCG), a live and attenuated strain of *Mycobacterium bovis*, is the only available vaccine against TB to date and has been used for the vaccination of newborns for decades. This vaccine has its limitations however, and progress in generating more effective TB vaccines has been made with several candidate vaccines in recent years. One candidate that has been in clinical trials is based on adenovirus serotype 35 expressing Ag85A, Ag85B and TB10.4 antigens of Mtb (Havenga et al., 2006; Radoševié et al., 2007; WO 2006/053871). This vaccine has been demonstrated to be safe in uninfected people and was able to induce high T-cell responses against Mtb antigens of the vaccine, making it a promising candidate for a prophylactic TB vaccine.

Vaccination in patients having active TB with the aim of treating these patients would, however, require a therapeutic TB vaccine. In principle, such a therapeutic TB vaccine might have the potential to improve therapy for active TB.

The concept of a therapeutic TB vaccine to cure tuberculosis was first coined by Robert Koch himself in 1890 when he announced the cure of tuberculosis by tuberculin therapy (see Burke, 1993). Tuberculin consists of extracts of Mtb.

However, although the treatment succeeded in curing the disease in some patients, a subset of patients exhibited worsening of symptoms, which became known as Koch's phenomenon. Koch's phenomenon occurs due to systemic release of Th1-associated cytokines, resulting in necrosis of TB lesions (Churchyard et al., 2009) that could lead to devastating clinical symptoms, which may even result in death. Thus, an important safety consideration that will need to be demonstrated for any new therapeutic TB vaccine candidate is the absence of Koch's phenomenon following widespread vaccine administration to TB patients. This can only be addressed by well-designed, controlled clinical trials in endemic areas.

In recent times, interest in reinvigorating therapeutic TB vaccination regained attention, particularly with the possibility for use as an adjunct to TB chemotherapy with the hope of shortening treatment. Animal studies have indicated that DNA vaccines encoding TB antigens such as heat shock protein 65 (HSP-65) (Lowrie et al., 1999), Ag85A (Ha et al., 2005) and Ag85B (Zhu et al., 2005) could reduce bacterial burden in Mtb-infected animals (Ha et al., 2005; Zhu et al., 2005), and prevent relapses when used in conjunction (Ha et al., 2005) or following the completion of chemotherapy (Lowrie et al., 1999).

A therapeutic TB vaccine, given when the bacterial burden is low, early in chemotherapy, should enable the immune system to target persisters, to result in the prevention of relapse. In clinical studies, a heat-killed environmental mycobacterial (*Mycobacterium vaccae*) preparation has been shown to be effective as an adjunctive treatment in MDR-TB as shown in trials conducted in China (Fan et al., 2007). This therapy relies on the non-specific nature of *M. vaccae* immunomodulation. Another vaccine in clinical development is RUTI, which is a liposome preparation containing cell wall of Mtb, aimed for usage as an adjunct to TB chemotherapy (Churchyard et al., 2009).

Despite the progress, an important safety consideration that still remains to be demonstrated for these vaccines is the absence of Koch's phenomenon following widespread vaccine administration to TB-infected patients, an important aspect that can only be addressed by well-designed, controlled clinical trials in endemic areas. Indeed, a few years ago it was reported in a conference by one company active in this field that development of a therapeutic vaccine candidate had to be discontinued for safety reasons. Furthermore, although some reports for treatment of TB using a DNA vaccine encoding hsp60 or Ag85 antigen in mice were successful, others reported classical Koch reactions in an immunotherapeutic mouse model (Taylor et al., 2003). This underscores the risk of eliciting Koch's phenomenon by immunotherapeutic vaccination, and thus highlights the need for clinical studies for each vaccine candidate to assess potential safety problems.

US 2004/0057963 relates to therapeutic vaccines against latent TB by delivering polypeptides or nucleic acids encoding such, which polypeptides are upregulated or expressed during the latent stage of mycobacteria infection. US 2004/0057963 teaches that some antigens (exemplified therein by ESAT6), though potent as prophylactic vaccine, have no effects as therapeutic vaccines, whereas, in contrast with other antigens (exemplified therein by Rv2031c), can be efficient therapeutic vaccines although they have no or only negligible effects as prophylactic vaccines (see, e.g., Example 2 therein). Thus, the skilled person consulting US 2004/0057963 is taught to use different antigens for therapeutic TB vaccines than for prophylactic TB vaccines.

A further complicating factor for therapeutic vaccination of patients with active TB, is that individuals with active TB actually possess T lymphocytes that are unresponsive to stimuli with antigens from Mtb, as observed by tetramer binding assays (Weichold et al., 2007). Indeed, the clinical trials described in the present invention demonstrate that the patients having active TB in these trials are "immunosuppressed" or "tolerant" with respect to at least some major Mtb antigens, although it is well known that, for instance, Ag85A and Ag85B are amongst the strongest immunogenic proteins of Mtb, the subjects did not have a response to these proteins. Thus, a therapeutic vaccine candidate should be capable of breaking this Mtb-induced tolerance on cell-mediated immunity.

Thus, the instant invention aims at providing therapeutic treatment of patients having active TB, which treatment should be effective yet comply with strict safety standards, and preferably should also be capable of being used in conjuction with drug therapy and preferably improve such drug therapy by shortening the duration thereof.

DISCLOSURE

The dislcosure is thus based on the novel idea that the reason TB persists clinically in treated and untreated individuals is that the Mtb *bacillus* is able to induce tolerance against what are normally immunodominant antigens of Mtb. The induction of such tolerance paralyzes the immune system in an antigen-specific manner so that it is not able to recognize and kill intracellular TB organisms that chemotherapeutic agents have little access to. By presenting these antigens in the context of an adenovector that inserts nucleic acids coding for these antigens into specific target cells, tolerance can be broken and effective antigen-specific responses can be induced. Furthermore, these antigen-specific responses are induced in a manner that does not induce the general inflammatory response associated with Koch's phenomenon. This invention is, therefore, able to break tolerance and induce antigen-specific immune responses, in the absence of deleterious non-specific inflammatory responses that lead to progression rather than suppression of disease. The tolerance is, for example, demonstrated in a clinical trial in humans being treated for active TB, who were surprisingly found to not have cellular immune responses to normally immunodominant antigens Ag85A and Ag85B, indicating tolerance to these antigens during the process of active infection. It was further shown that immunization with a recombinant adenoviral vector containing nucleic acid coding for Ag85A and Ag85B surprisingly could break this tolerance and induce high levels of cellular immunity in these individuals that demonstrated lack of immune response to these immunodominant antigens during TB infection. It was also surprisingly shown that the induction of this antigen-specific immune response in this manner did not cause any signs of Koch's phenomenon or clinical progression of pulmonary or other forms of TB in these individuals undergoing chemotherapy for active disease. The type of cellular immunity induced in these patients was primarily CD8 T cells expressing gamma interferon, which suggests effector memory cells capable of killing TB inside infected cells.

One of the front runners in the race to find new prophylactic TB vaccine candidates is an adenovirus-based TB vaccine expressing the TB antigens Ag85A, Ag85B and TB10.4 inside host cells as a fusion protein, called Ad35.TBS or Ad35.TB-S (Havenga et al., 2006; Radošević et al., 2007; WO 2006/053871; the vaccine is also referred to as AERAS-402 in literature), and this candidate is undergoing extensive Phase I and II clinical trials in Africa and the USA. In order to proceed to larger clinical trials in the future without the need for extensive TB testing among recruits for practical reasons, it was decided to first test the safety of the vaccine in Mtb-infected individuals. Therefore, a clinical trial for this vaccine was conducted in South Africa. The vaccine was tested in a Phase II trial among people undergoing TB therapy as well as those who are cured but were previously infected with TB.

The surprising results of this study demonstrated that the vaccine was safe by the notable absence of Koch's phenomenon in Mtb-exposed individuals. Equally crucially, the vaccine was able to overcome the immune suppression to Mtb antigens mediated by the bacteria, as measured by the immunological responses to the vaccine antigens. These clinical trial findings reveal the enormous potential for the utilization of a recombinant adenovirus vector that comprises nucleic acid encoding the Mtb antigens Ag85A, Ag85B and TB10.4 in a therapeutic setting. The vaccine may also be used as an adjunct to antibiotics, for example, to shorten the duration of TB drug therapy, and/or to reduce the relapse rates of shortened TB drug therapy treatment regimens.

Thus, the invention in a first aspect provides a method for treatment of a patient having active tuberculosis (TB), the method comprising: administering to the patient a recombinant adenovirus vector that comprises nucleic acid encoding the Ag85A, Ag85B and TB 10.4 antigens of *Mycobactium tuberculosis* (Mtb).

Further provided is a method for inducing an immune response against antigens of Mtb in a subject infected with Mtb, the method comprising administering to the subject administering to the patient a recombinant adenovirus vector that comprises nucleic acid encoding the Ag85A, Ag85B and TB 10.4 antigens of Mtb to express the antigens and induce an immune response to at least one of the antigens in the subject.

In a third aspect, provided is a recombinant adenovirus vector that comprises nucleic acid encoding the Ag85A, Ag85B and TB 10.4 antigens of Mtb for the treatment of patients having active TB.

In a fourth aspect, provided is a recombinant adenovirus vector that comprises nucleic acid encoding the Ag85A, Ag85B and TB10.4 antigens of Mtb for inducing an immune response against antigens of Mtb in a subject infected with Mtb.

In a fifth aspect, provided is the use of a recombinant adenovirus vector that comprises nucleic acid encoding the Ag85A, Ag85B and TB10.4 antigens of Mtb for the preparation of a medicament for the treatment of patients having active TB.

In a sixth aspect, provided is the use of a recombinant adenovirus vector that comprises nucleic acid encoding the Ag85A, Ag85B and TB10.4 antigens of Mtb for the preparation of a medicament for inducing an immune response against antigens of Mtb in a subject infected with Mtb.

The following embodiments relate to each of the aspects hereof described above, unless it is clear from the context that the embodiment relates to certain aspects only.

In certain embodiments, the patient or subject is subjected to drug therapy, e.g., by administering to the patient or subject one or more antibiotic drugs that are capable of killing Mtb. In further embodiments, the patient or subject is on treatment or eligible for treatment by drug therapy.

In certain embodiments, the patient or subject is subjected to drug therapy for a reduced period as compared to standard drug therapy, e.g., the administering of antibiotic drugs is performed in a regimen that is shorter than a standard regimen of administering the antibiotic drugs to which the patient or subject would be eligible in the absence of administering the adenovirus.

In certain embodiments, subjecting the patient to drug therapy for a reduced period comprises administering therapeutic drugs such as antibiotic drugs to the patient for a period of about between one week and five months, e.g., between two weeks and four months.

In certain embodiments, the standard drug therapy regimen for the patient comprises the daily administration of a cocktail of isoniazid, rifampin, pyrazinamide and ethambutol for a period of two months, followed by administration of rifampin and isoniazid with or without ethambutol daily or three times per week for a period of four months.

In certain embodiments, the bacterial burden of Mtb as measured in a group of patients at a given time after the initiation of drug therapy is lower as compared to the burden at the same time point without the administration of the adenovirus.

In certain embodiments, the relapse rate of active TB as measured in a population of patients after the therapeutic drug therapy for a reduced period is the same as or less than for a standard drug regimen for a normal period without the administration of the adenovirus.

In certain embodiments, the nucleic acid encoding Ag85A, Ag85B and TB 10.4 antigens, encodes these antigens as a fusion protein.

In certain embodiments, the adenovirus is a replication-deficient human adenovirus of serotype 35.

In certain embodiments, the adenovirus is a replication-deficient human adenovirus of serotype 26.

In certain embodiments, the adenovirus vector is administered in a heterologous prime-boost regimen. In certain embodiments, the heterologous prime-boost regimen comprises administration of vectors of human adenovirus serotype 35 and of human adenovirus serotype 26.

In certain embodiments, the TB that the patient has is pulmonary TB.

In certain embodiments, the patient or subject has an infection with multidrug-resistant Mtb (MDR-TB) or extremely drug-resistant Mtb (XDR-TB).

In certain embodiments, a recombinant adenovirus vector that comprises nucleic acid encoding the Ag85A, Ag85B and TB 10.4 antigens of Mtb is administered to the patient or the subject more than once.

In certain embodiments, the administration of the recombinant adenovirus vector induces a CD8+ T-cell response in the patient or the subject against at least one of the antigens encoded by the nucleic acid in the adenovirus.

In certain embodiments, the CD8+ T-cell response is a polyfunctional T-cell response.

In certain embodiments, the administration of the recombinant adenovirus vector induces a CD4+ T-cell response in the patient or the subject against at least one of the antigens encoded by the nucleic acid in the adenovirus.

In certain embodiments, the subject that is infected with Mtb has latent TB.

DETAILED DESCRIPTION

Figure 1:
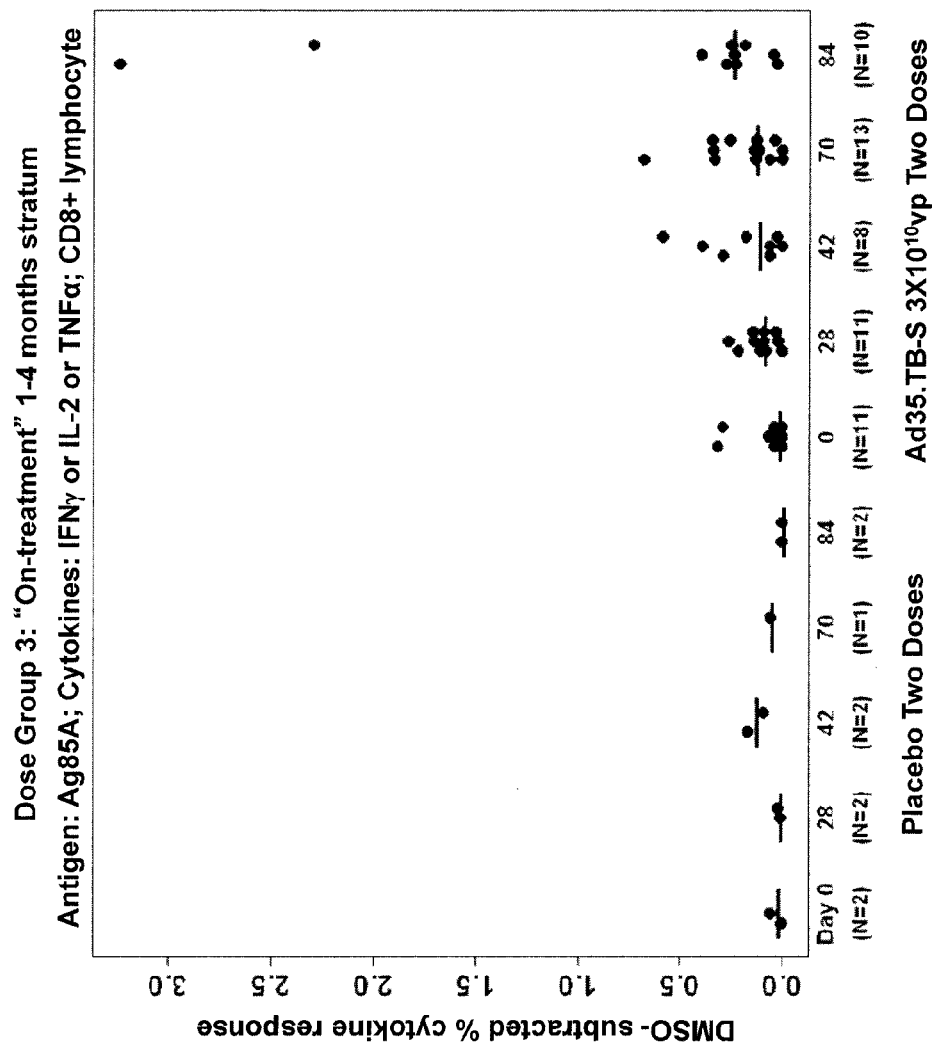
FIG. 1. Increase in the percentage of CD8 lymphocytes over time-releasing IFNγ or IL-2 or TNF-α upon stimulation with pooled peptides of Ag85A among vaccinees receiving $3\times10^{10}$ virus particles (vp) when compared to placebo control.

TB can be either latent or active, as is known to the skilled person and can be detected and recognized according to routine methods known to the skilled person, such as radiographic, bacteriologic or immunologic methods or combinations thereof (see, e.g., Mitchison, 2005). Examples are acid-fast *bacillus* (AFB) smear of sputum samples, mycobacterial culture, tuberculin skin testing and interferon-γ release assays. For instance, AFB or mycobacterial culture can also be used to determine the effects of therapy. Latent TB means that the Mtb bacteria are present in the body of a subject, but the body's defenses are keeping it from turning into active TB. This means that such subjects do not have any symptoms at that moment and normally don't spread the disease to others. Latent TB can become active TB at some stage. Active TB means that the Mtb bacteria are growing and causing symptoms. Infection often takes place in the lungs, and this is called pulmonary TB. If the lungs are infected with active TB, the disease can easily be spread to others. TB can also spread to other parts of the body, which is called extra-pulmonary TB. Extra-pulmonary TB may include disseminated tuberculosis, lymphatic tuberculosis, pleural tuberculosis, genitourinary tuberculosis, bone and joint tuberculosis and central nervous system tuberculosis. The invention is in principle suitable for improving therapy of any sort of active TB. In certain embodiments, the active TB hereof is pulmonary TB. Infection with HIV increases the likelihood to get TB and, hence, in certain embodiments, the TB patient may also have concomitant infection with HIV. In other embodiments, the TB patient does not have concomitant HIV infection. Symptoms of active TB may include: a cough that brings up thick, cloudy and sometimes bloody mucus from the lungs (called sputum) for more than two weeks, tiredness and weight loss, night sweats and a fever, a rapid heartbeat, swelling in the neck (when lymph nodes in the neck are affected), shortness of breath and chest pain (in rare cases). Pulmonary TB is usually diagnosed by taking a sample of sputum and testing whether there are Mtb bacteria in it. Sometimes a chest radiograph is taken to help find pulmonary TB. Extrapulmonary TB can be found using biopsy or fluid aspiration of the infected tissue, or collection of excretions, for AFB smear, culture and histology.

In preferred embodiments hereof, a patient hereof is a human patient. In other embodiments, the patient may be a mammal that is capable of being infected with Mtb and in certain aspects having active TB, for example, a domestic animal, or a rodent such as a mouse, in a model for TB.

An adenovirus is used as a therapeutic vaccine herein. Adenoviruses for therapeutic or prophylactic vaccines are well known and can be manufactured according to methods well known to the skilled person. An adenoviral vector can be generated by using any species, strain, subtype, or mixture of species, strains, or subtypes, of an adenovirus or a chimeric adenovirus as the source of vector DNA (see, for instance, WO 96/26281, WO 00/03029). An adenovirus hereof preferably is a human adenovirus. It can be of any serotype. Human adenoviral vectors that were identified to be particularly useful are based on serotypes 11, 26, 34, 35, 48, 49, and 50 as was shown in WO 00/70071, WO 02/40665 and WO 2004/037294. Others have found that also adenovirus 24 (Ad24) is of particular interest as it is shown to be a rare serotype (WO 2004/083418). In a preferred embodiment, the adenovirus used for the invention is thus a human adenovirus of a serotype selected from the group consisting of: Ad11, Ad24, Ad26, Ad34, Ad35, Ad48, Ad49 and Ad50. The advantage of this selection of human adenoviruses as vaccine vectors is that humans are not regularly infected with these wild-type adenoviruses, so that neutralizing antibodies against these serotypes are less prevalent in the human population at large. Particularly preferred serotypes hereof are Ad35 and Ad26. In another preferred embodiment, the adenovirus is a simian, canine or a bovine adenovirus, since these viruses also do not encounter pre-existing immunity in the (human) host to which the recombinant virus is to be administered. The applicability of simian adenoviruses for use in human gene therapy or vaccines is well appreciated by those of ordinary skill in the art. Besides this, canine and bovine adenoviruses were found to infect human cells in vitro and are, therefore, also applicable for human use. Particularly preferred simian adenoviruses are those isolated from chimpanzee. Examples that are suitable include C68 (also known as Pan 9; U.S. Pat. No. 6,083,716) and Pan 5, 6 and 7 (WO 03/046124); see also WO 03/000851.

Recombinant adenoviruses can be produced to very high titers using cells that are considered safe, and that can grow in suspension to very high volumes, using medium that does not contain any animal- or human-derived components. Also, it is known that recombinant adenoviruses can elicit a dramatic immune response against the protein encoded by the heterologous nucleic acid sequence in the adenoviral genome.

In the genome of the adenovirus, the nucleic acid encoding the transgene(s), here the Ag85A, Ag85B and TB10.4 antigens, is operably linked to expression control sequences. This can, for instance, be done by placing the nucleic acid encoding the transgenes under the control of a promoter. Further regulatory sequences may be added. A convenient and routine way of doing this is cloning the transgenes into an expression cassette, available in many formats from several expression plasmids sold by commercial vendors, which expression cassette usually contains sequences capable of bringing about expression of the nucleic acid, such as enhancer(s), promoter, polyadenylation signal, and the like. Several promoters can be used for expression of the transgenes, and these may comprise viral, mammalian, synthetic promoters, and the like. Non-limiting examples of suitable promoters for obtaining expression in eukaryotic cells are the CMV-promoter (U.S. Pat. No. 5,385,839), a mammalian EF1-alpha promoter, a mammalian ubiquitin C promoter, or a SV40 promoter. In certain embodiments, a promoter driving the expression of the transgenes is the CMV immediate early promoter, for instance, comprising nt. −735 to +95 from the CMV immediate early gene enhancer/promoter. A polyadenylation signal, for example, the bovine growth hormone polyA signal (U.S. Pat. No. 5,122,458), may be present behind the transgenes.

The administration of the adenovirus hereof will result in expression of the Ag85A, Ag85B and TB10.4 antigens in cells of the patient to which the adenovirus is administered. This will result in an immune response to at least one of the antigens in the patient. Thus, the invention provides methods and uses hereof, wherein the nucleic acid encoding the Ag85A, Ag85B and TB10.4 antigens is expressed in the patient. In certain aspects, the invention provides methods and uses hereof, so that an immune response against at least one, preferably at least two, more preferably all three of the Ag85A, Ag85B and TB 10.4 antigens is induced.

Preferably, the adenoviral vector is deficient in at least one essential gene function of the E1 region, e.g., the E1a region and/or the E1b region, of the adenoviral genome that is required for viral replication. In certain embodiments, the vector is deficient in at least one essential gene function of the E1 region and at least part of the non-essential E3 region. The adenoviral vector can be "multiply deficient," meaning that the adenoviral vector is deficient in one or more essential gene functions in each of two or more regions of the adenoviral genome. For example, the aforementioned E1-deficient or E1-, E3-deficient adenoviral vectors can be further deficient in at least one essential gene of the E4 region and/or at least one essential gene of the E2 region (e.g., the E2A region and/or E2B region). As known to the skilled person, in case of deletions of essential regions from the adenovirus genome, the functions encoded by these regions have to be provided in trans, preferably by the producer cell, i.e., when parts or whole of E1, E2 and/or E4 regions are deleted from the adenovirus, these have to be present in the producer cell, for instance, integrated in the genome, or in the form of so-called helper adenovirus or helper plasmids.

In certain embodiments, the adenovirus hereof lacks at least a portion of the E1-region, e.g., E1A and/or E1B coding sequences, and further comprises heterologous nucleic acid encoding the Mtb antigens Ag85A, Ag85B and TB10.4.

The construction of adenoviral vectors is well understood in the art and involves the use of standard molecular biological techniques, such as those described in, for example, Sambrook et al., *Molecular Cloning, a Laboratory Manual,* 2d ed., Cold Spring Harbor Press, Cold Spring Harbor, N.Y. (1989); Watson et al., *Recombinant DNA,* 2d ed., Scientific American Books (1992); and Ausubel et al., *Current Protocols in Molecular Biology*, Wiley Interscience Publishers, NY (1995), and other references mentioned herein.

Adenoviral vectors, methods for construction thereof, and methods for propagating thereof, are well known in the art and are described in, for example, U.S. Pat. Nos. 5,559,099, 5,837,511, 5,846,782, 5,851,806, 5,994,106, 5,994,128, 5,965,541, 5,981,225, 6,040,174, 6,020,191, and 6,113,913, and Thomas Shenk, "Adenoviridae and their Replication," M. S. Horwitz, "Adenoviruses," Chapters 67 and 68, respectively, in *Virology*, B. N. Fields et al., eds., 3d ed., Raven Press, Ltd., New York (1996), and other references mentioned herein.

In preferred embodiments, the adenovirus is replication deficient, e.g., because it contains a deletion in the E1 region of the genome. If the adenovirus is an adenovirus from a subgroup other than human adenovirus subgroup C (e.g., Ad35 from subgroup B or Ad26 from subgroup D), it is preferred to exchange the E4-orf6 coding sequence of the adenovirus with the E4-orf6 of an adenovirus of human subgroup C such as Ad5. This allows propagation of such adenoviruses in well-known complementing cell lines that express the E1 genes of Ad5, such as, for example, 293 cells, PER.C6® cells, and the like (see, e.g. Havenga et al., 2006; WO 03/104467, incorporated in its entirety by reference herein). In certain embodiments, the adenovirus is a human adenovirus of serotype 35, with a deletion in the E1 region into which the nucleic acid encoding the antigens has been cloned, and with an E4 orf6 region of Ad5. In other embodiments, the adenovirus is a human adenovirus of serotype 26, with a deletion in the E1 region into which the nucleic acid encoding the antigens has been cloned, and with an E4 orf6 region of Ad5. If the adenovirus is of human subgroup B, such as Ad35, Ad34 or Ad11, it is preferred to retain the 3' end of the E1B 55K open reading frame in the adenovirus, for instance, the 166 bp directly upstream of the pIX open reading frame or a fragment comprising this, such as a 243 bp fragment directly upstream of the pIX start codon, marked at the 5' end by a Bsu36I restriction site, since this increases the stability of the adenovirus because the promoter of the pIX gene is partly residing in this area (see, e.g. Havenga et al., 2006; WO 2004/001032, incorporated by reference herein).

The adenovirus used hereinherein comprises Ag85A, Ag85B and TB10.4 antigens of Mtb. Such adenoviruses and ways of making these have been described before in Havenga et al., 2006; Radošević et al., 2007; WO 2006/053871, all incorporated in their entirety by reference herein. In certain embodiments, the adenovirus hereof comprises nucleic acid encoding the Ag85A, Ag85B and TB10.4 antigens as a fusion protein. In certain embodiments, the nucleic acid encodes the entire open reading frames of the Ag85A, Ag85B and TB10.4 antigens in that 5' to 3' order, as a fusion protein. In other embodiments, the adenovirus comprises fragments of the coding sequences for the Ag85A, Ag85B and/or TB10.4 antigens, which fragments comprise antigenic parts or epitopes of these Mtb proteins. In certain embodiments the adenovirus comprises nucleic acid encoding the fusion protein as provided by amino acids 1-676 of SEQ ID NO:7 of US 2009/0123438 A1, incorporated in its entirety by reference herein. In certain embodiments, the nucleic acid sequence encoding the antigens has been codon optimized for expression in humans. In certain embodiments, the adenovirus comprises a nucleic acid sequence comprising nucleotides 13-2043 of SEQ ID NO:4 of US 2009/0123438 A1, incorporated in its entirety by reference herein.

The adenovirus used hereinherein was thus already known as a prophylactic vaccine against TB, and the instant invention discloses for the first time its use as a therapeutic vaccine in patients with active TB. This use could not be anticipated and is surprising, since there appears an induced tolerance generated by Mtb on host cellular immunity toward Mtb antigens (Weichold et al., 2007), as further shown for the Ag85A and Ag85B antigens in the clinical trial described hereinbelow, a tolerance that was surprisingly found to be broken by the vaccine hereof. A further reason why this could not be predicted is that antigens that are useful as prophylactic TB antigens are not necessarily effective as therapeutic TB antigens (see, e.g., Andersen et al., in US 2004/0057963), underscoring the unpredictability of the immune responses for these vaccines.

Adenoviruses can be prepared, harvested and purified in cell culture systems well known in the art and, for instance, WO 2010/060719, incorporated by reference herein, describes suitable methods for obtaining and purifying large amounts of recombinant adenoviruses such as those used in the present invention. Further methods for producing and purifying adenoviruses are disclosed in, for example, WO 98/22588, WO 00/32754, WO 04/020971, U.S. Pat. No. 5,837,520, U.S. Pat. No. 6,261,823, WO 2005/080556, and WO 2006/108707, all incorporated by reference herein.

For administering to humans, the invention may employ pharmaceutical compositions comprising the adenovirus and a pharmaceutically acceptable carrier or excipient. In the present context, the term "pharmaceutically acceptable" means that the carrier or excipient, at the dosages and concentrations employed, will not cause unwanted or harmful effects in the subjects to which they are administered. Such pharmaceutically acceptable carriers and excipients are well known in the art (see *Remington's Pharmaceutical Sciences,* 18th edition, A. R. Gennaro, Ed., Mack Publishing Company [1990]; *Pharmaceutical Formulation Development of Peptides and Proteins*, S. Frokjaer and L. Hovgaard, Eds., Taylor & Francis [2000]; and *Handbook of Pharmaceutical Excipients,* 3rd edition, A. Kibbe, Ed., Pharmaceutical Press [2000]). The purified adenovirus preferably is formulated and administered as a sterile solution. Sterile solutions are prepared by sterile filtration or by other methods known per se in the art. The solutions can then be lyophilized or filled into pharmaceutical dosage containers. The pH of the solution generally is in the range of pH 3.0 to 9.5, e.g., pH 5.0 to 7.5. The adenovirus or immunogenic parts thereof typically are in a solution having a suitable pharmaceutically acceptable buffer, and the solution of adenovirus may also contain a salt. In certain embodiments, detergent is present. In certain embodiments, the vaccine may be formulated into an injectable preparation. These formulations contain effective amounts of the adenovirus, are either sterile liquid solutions, liquid suspensions or lyophilized versions and optionally contain stabilizers or excipients. The vaccine can also be aerosolized for intranasal administration (see, e.g., WO 2009/117134).

For instance, the adenovirus may be stored in the buffer that is also used for the Adenovirus World Standard (Hoganson et al., Development of a stable adenoviral vector formulation, *Bioprocessing* March 2002, p. 43-48): 20 mM Tris pH 8, 25 mM NaCl, 2.5% glycerol. Another useful formulation buffer suitable for administration to humans is 20 mM Tris, 2 mM $MgCl_2$, 25 mM NaCl, sucrose 10% w/v, polysorbate-80 0.02% w/v. Obviously, many other buffers can be used, and several examples of suitable formulations for the storage and for pharmaceutical administration of purified (adeno)virus preparations can, for instance, be found in European patent no. 0853660, U.S. Pat. No. 6,225,289 and in international patent applications WO 99/41416, WO 99/12568, WO 00/29024, WO 01/66137, WO 03/049763, WO 03/078592, WO 03/061708.

In certain embodiments, the vaccine further comprises an adjuvant. Adjuvants are known in the art to further increase the immune response to an applied antigenic determinant, and pharmaceutical compositions comprising adenovirus and adjuvants are, for instance, disclosed in WO 2007/110409, incorporated by reference herein. Examples of suitable adjuvants include aluminium salts such as aluminium hydroxide and/or aluminium phosphate; oil-emulsion compositions (or oil-in-water compositions), including squalene-water emulsions, such as MF59 (see, e.g., WO 90/14837); saponin formulations, such as, for example, QS21 and Immunostimulating Complexes (ISCOMS) (see, e.g., U.S. Pat. No. 5,057,540; WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as *E. coli* heat labile enterotoxin LT, cholera toxin CT, pertussis toxin PT, or tetanus toxoid TT. Examples of further adjuvants are given in WO 2007/110409.

In other embodiments, the vaccines used herein do not comprise further adjuvants.

In the methods or uses hereof, the dose of the adenovirus provided to a patient during one administration can be varied as is known to the skilled practitioner, and is generally between $1 \times 10^7$ viral particles (vp) and $1 \times 10^{12}$ vp, preferably between $1 \times 10^8$ vp and $1 \times 10^{11}$ vp, for instance, between $3 \times 10^8$ and $5 \times 10^{10}$ vp, for instance, between $10^9$ and $3 \times 10^{10}$ vp.

Administration of the vaccine hereof can be performed using standard routes of administration. Non-limiting embodiments include parenteral administration, such as by injection, e.g., into the blood stream, intradermal, intramuscular, etc., or mucosal administration, e.g., intranasal, oral, and the like. In one embodiment, the vaccine is administered by intramuscular injection into the deltoid muscle. The skilled person knows the various possibilities to administer a vaccine hereof, in order to induce an immune response to at least one of the antigens in the vaccine.

A patient with active TB is treated by administering the adenovirus hereof, which is referred to as immunotherapy or thereapeutic vaccination. Treatment as used herein is therapeutic treatment, i.e., with the aim of improving the condition of the patient, preferably resolving the TB completely. The treatment hereof involves immunotherapeutic vaccination, i.e., it aims at inducing an immunogenic response against at least one of the Ag85A, Ag85B and TB10.4 antigens, preferably against at least two of these, more preferably against all three of these. In preferred embodiments, the treatment reduces the level of the Mtb infection in the patient. In preferred embodiments, the treatment results in curing the patient from active TB, more preferably the treatment finally results in absence of infection with Mtb in the patient.

In contrast, the prior art use of similar vaccines aimed at prevention or prophylaxis of TB, by administering the vaccine to subjects that were not infected with Mtb and/or had no active TB. Immune responses and potential effects thereof in such cohorts can be very different, and not predictive for the effects of immunotherapy in Mtb-infected patients, especially patients with active TB.

In certain aspects, therefore, provided is a method for inducing an immune response against antigens of Mtb in a subject infected with Mtb, the method comprising administering to the subject a recombinant adenovirus vector that comprises nucleic acid encoding the Ag85A, Ag85B and TB10.4 antigens of Mtb to express the antigens and induce an immune response to at least one of the antigens in the subject.

It is an aspect hereof to provide such methods for treating patients having active TB.

In certain aspects hereof, the subject or patient is further treated by administering to the subject or patient one or more drugs that are capable of killing or at least significantly inhibiting the growth of Mtb. Thus, also provided is a combination of immunotherapy with drug therapy, with the aim to prevent the subject from developing or to cure the patient from active TB, preferably to remove any infection of Mtb from the subject or patient.

Clinical trials with a vaccine hereof in groups of patients infected with Mtb and either having latent or active TB have demonstrated that the immunotherapeutic vaccination according to the present invention does not lead to Koch's phenomenon. Koch's phenomenon is thought to occur due to boosting of Th1 responses leading to a release of Th1-related cytokines triggering necrosis of lesions containing Mtb (Churchyard et al., 2009). Many TB patients treated by Robert Koch with tuberculin suffered from systemic reactions such as delirium, coma or angina pectoris (Burke, 1993). In some cases, deaths occurred in patients with advanced cavitary pulmonary disease (Burke, 1993).

Active TB is usually treated with drug therapy. Drug treatment of TB aims to reduce the Mtb burden by sterilization and prevention of disease relapse following therapy. The largest number of drugs are utilized in the initial phase of therapy to prevent resistant strains emerging when the bacterial population is at its largest (D. A. Mitchison, 2005). The risk of drug resistance reduces as the bacillary burden lowers over time. Thus, the remainder of TB therapy utilizes fewer drug combinations compared to the initial phase of treatment (D. A. Mitchison, 2005).

"Drug therapy" as used herein comprises the administration of one or more antibiotics to the patient, usually a combination of such antibiotics. These antibiotics are capable of killing or at least significantly inhibiting the growth of Mtb. Several such antibiotics are known and available to the skilled person, which is capable of making the best choice amongst those for the case of each individual patient. Usually, a treatment regime takes six months, with daily administration of antibiotics. If tests still show an active TB infection after six months, the treatment is continued for another two or three months. DOT may be used to help the patient follow all the instructions and keep up with the treatment that can be complex and takes a long time. It is recommended to use more than one medicine to prevent MDR-TB. Antibiotics useful in the drug therapy for treating active TB include isoniazid, rifampin, pyrazinamide, and ethambutol. Further antibiotics useful in treatment include p-aminosalicylic acid, streptomycin, thiacetazone, fluoroquinolones, PA 824, R207910, rifabutin, rifapentine, amikacin, capreomycin, cycloserine, ethionamide, levofloxacin, and moxifloxacin. The dose to be administered for each antibiotic is generally well known to the skilled person, and generally is at least as high as the minimal effective dose that gives bactericidal activity (see, e.g., Mitchison, 2005). The standard treatment begins with four medicines given daily for two months. The first two months of therapy known as the initiation phase, consists of isoniazid, rifampin, pyrazinamide and ethambutol taken daily. In certain regimens, streptomycin is used instead of ethambutol, especially for people who cannot take ethambutol, but generally ethambutol is preferred, to avoid transmission of HIV. The next phase, termed the continuation phase, reduces the therapy to rifampin and isoniazid, on a daily or three times per week basis. In certain cases, ethambutol is also added during this phase. This phase takes four months in standard regimens. In some cases, this phase is lengthened to nine months or even longer if necessary. The number of medicines used during this time depends on the results of sensitivity testing. Another standard regimen consists of an eight-month regimen, wherein in a two-month initiation phase, isoniazid, rifampin, pyrazinamide and streptomycin is used, continuing with thiacetazone and isoniazid for six months; for this regimen sometimes ethambutol is substituted for thiacetazone as well as for streptomycin. If required, a different combination of medicines is tried if the treatment is not working because of drug resistance, when tests show that TB-causing bacteria are still active. Relapses may occur if treatment has not been successful, and such relapses usually occur within six to twelve months after treatment. Treatment after relapse is based on the severity of the disease and which medicines were used during the first treatment.

Thus, standard treatment may differ for different patients, but still is standard treatment hereof, as it is well known and routine for the skilled practitioner to decide which treatment is needed in individual cases depending on the circumstances. Such a practitioner can follow the recommendations of the WHO regarding the standard drug therapy for TB. Several regimes for treatment of active TB are reviewed in Mitchison (2005), incorporated by reference herein.

The standard drug therapy treatment can thus be significantly shortened by the methods of the present invention. In certain embodiments, the therapeutic vaccination hereof may render drug therapy redundant, but generally, the drug therapy treatment hereof will take at least one week, at least two weeks, or at least three weeks. In certain embodiments, the administration of drugs can be shortened by at least one month, at least two months, or more, as compared to a standard drug therapy regimen. In certain preferred embodiments, the standard drug therapy regimen hereof comprises the daily administration of a cocktail of isoniazid, rifampin, pyrazinamide and ethambutol for a period of two months, followed by administration of rifampin and isoniazid with or without ethambutol daily or three times per week for a period of four months, and the standard drug therapy treatment can be shortened to a total period of less than five months, four months or less, three months or less, two months or less, six weeks or less, five eeks or less, or four weeks or less. This can be established by shortening either the continuation or the initiation phase, or both. It may also be possible to administer less amounts of drugs, less different drugs of the cocktail, or less frequently than normal. Clearly, this is a breakthrough in the therapy of active TB, since it significantly shortens the period during which therapeutic drugs need to be taken by the patient, which results in lower costs and importantly reduces the logistic burden and complexity of the treatment. In principle, the drug treatment becomes more akin to standard antibiotic treatments of other diseases.

Using the methods hereof, DOT is required for more limited periods compared to standard drug treatment of active TB, and in preferred embodiments, DOT is no longer required at all. Without wishing to be bound by theory, it is hypothesized that the methods hereof break the tolerance of the patient, so that the immune system will be capable of removing the residual Mtb bacteria after the vast majority thereof has been killed by the therapeutic drug regimen, like the immune system generally does for other bacteria after antibiotic treatment. When measured over a population of patients, this results in a significantly reduced relapse rate of active TB, when measured after, for instance, six to 24 months after treatment with the drug regimen. The standard regimen has a relapse rate of between about 0-2%. If a standard drug regimen is shortened to four months, the relapse proportion at 24 months is between 8 to 11.8% (Clinical trial of 6-month and 4-month regimens of chemotherapy in the treatment of pulmonary tuberculosis, 1981).

In preferred embodiments, the instant invention comprises administering the therapeutic vaccine hereof in conjunction with therapeutic drug administration for a period that is significantly reduced compared to the standard period for drug administration, resulting in a significantly reduced relapse rate as compared to the relapse rate that is observed for the same drug therapy without the therapeutic vaccination. Preferably, the relapse rate at the shortened drug therapy regimen hereof is about the same or lower than the relapse rate of the standard drug therapy regimen of six months. In further embodiments, the immunotherapeutic vaccination hereof combined with drug therapy result in a decrease of the bacterial burden at a given time as compared to the same burden after the same drug therapy regimen without the immunotherapeutic vaccination.

The relapse rate can, for instance, be measured as the bacteriological relapse rate, measured by positive sputum culture at a specific time, e.g., at 24 months or 5 years after initiation or ending drug therapy.

The administration of the therapeutic vaccine hereof can, in principle, be performed before, but because of lower bacterial burden, preferably is performed during or after the therapeutic drug regimen, the "therapeutic drug regimen" in this case referring to the period of generally several months during which antibiotics are administered. In certain preferred embodiments, the vaccine is administered within 0 to 4 months after initiation of drug treatment, e.g., about 1 week, or about 2, 3, 4, 5, or 6 weeks, or about 2 months, or about 3 months, or about 4 months after initiation of drug treatment. In other embodiments, the vaccine is administered more than 4 months after initiation of drug treatment, e.g., more than 5, 6, 7, 8, or 9 months after initiation of drug treatment, and may even be administered after drug treatment has been ceased, e.g., one year or more after initiation of drug treatment, e.g., to prevent relapse of active TB. In other embodiments, the vaccine may also be administered at the indicated time points to subjects with past infection but diagnosed with latent TB.

In certain embodiments, the vaccine is administered more than one time, i.e., a prime-boost regimen for administration of the therapeutic vaccine is used. In cases where the vaccine is administered more than once, the timing of administration of the vaccine with respect to the therapeutic drug administration as described above refers to the first dose of the vaccine. In certain embodiments, where the vaccine is administered more than once, the administration of the second dose of the vaccine can be performed one week or more after the administration of the first dose of the vaccine, two weeks or more after the administration of the first dose of the vaccine, three weeks or more after the administration of the first dose of the vaccine, one month or more after the administration of the first dose of the vaccine, six weeks or more after the administration of the first dose of the vaccine, two months or more after the administration of the first dose of the vaccine, three months or more after the administration of the first dose of the vaccine, four months or more after the administration of the first dose of the vaccine, etc., up to several years after the administration of the first dose of the vaccine. In certain embodiments, the second dose of the vaccine is administered 42 days after the administration of the first dose of the vaccine. In embodiments where more than one dose of vaccine is administered, the vaccines may be heterologous with respect to each other, for instance, by using different adenovirus serotypes for the prime and the boost vaccination (see, e.g., WO 04/037294), e.g., priming with human Ad35 and boosting with human Ad26, priming with human Ad26 and boosting with Ad35, etc. This is referred to as a heterologous prime-boost regimen. The vectors of the different adenovirus serotypes then preferably are each a vector hereof, i.e., comprise nucleic acid encoding the Ag85A, Ag85B and TB10.4 antigens. It is also possible to use a different vector for priming or boosting, e.g., priming with adenovirus hereof and boosting with, for instance, DNA or MVA encoding the same or other TB antigens, or vice versa. Also, the priming and boosting vaccine may differ in the Mtb antigens, for instance, by omitting one or more of the Ag85A, Ag85B or TB10.4 antigens from the adenovirus hereof for either the priming or the boosting vaccine. In other embodiments, the vaccines may be homologous with respect to each other, i.e., the same vaccine is administered as prime and as boost vaccine. It is also possible to administer the vaccine more than twice, e.g. three times, four times, etc., so that the first priming administration is followed by more than one boosting administration. In addition, the therapeutic vaccine hereof may be used even after priming with BCG or recombinant forms of BCG, which may have been used to vaccinate the patient earlier in life. In other embodiments, the vaccine hereof is administered only once.

It has been observed that the administration of the vaccine hereof to patients having active TB, hereof, gives rise to CD8+ T-cell responses to Mtb antigens encoded by the vaccine. In certain aspects, therefore, methods and uses are provided, wherein the administration of the recombinant adenovirus vector induces a CD8+ T-cell response in the patient against at least one of the antigens encoded by the adenovirus vector, meaning that the patient has CD8 lymphocytes releasing cytokines, such as, for example, IL-2, IFN-γ or TNF-α. In certain embodiments, the CD8+ T-cell responses are boosted after a second administration of recombinant adenovirus vector. In certain embodiments, the CD8+ T-cell responses are polyfunctional, meaning that T lymphocytes secrete more than one cytokine. Such polyfunctional T lymphocytes may increase the efficiency of the treatments hereof. It has also been observed that the administration of the vaccine hereof gave rise to CD4+ T-cell responses to Mtb antigens encoded by the vaccine, in particular, after boosting with a second dose of adenovirus. In certain aspects, therefore, methods and uses are provided, wherein the administration of the recombinant adenovirus vector induces a CD4+ T-cell response in the patient against at least one of the antigens encoded by the adenovirus vector, meaning that the patient has CD4 lymphocytes releasing cytokines, such as, for example, IL-2, IFN-γ or TNF-α. In certain embodiments, the CD4+ T-cell responses are boosted after a second administration of recombinant adenovirus vector. Methods for measuring antigen-specific cellular immune responses such as CD8+ and CD4+ T-cell responses are well known and routine to the skilled person, and include, for instance, ELISPOT, intracellular cytokine staining (ICS), and multiplex cytokine assays (see, e.g., Havenga et al., 2006; Radošević et al., 2007; Lemckert et al., 2005; O'Connor, 2004).

Multidrug-resistant TB (MDR-TB) is defined as resistant to rifampin and isoniazid (WHO definition). Extremely drug-resistant TB (XDR-TB) is defined as resistant to any fluoroquinolone, and at least one of three injectable second-line drugs (capreomycin, kanamycin and amikacin), in addition to MDR-TB. Strategies to treat MDR-TB/XDR-TB differ according to the results of drug susceptibility testing and should contain at least four drugs with either certain, or almost certain, clinical effectiveness. The therapy involves an injectable drug phase of six to ten months followed by an oral drug therapy that result in a total duration of therapy of 18-24 months (WHO). The immunotherapeutic vaccination hereof prevents the return of TB after therapy, in particular, the return of TB caused by (multi-)drug-resistant forms of Mtb. The vaccination is also suitable to treat active TB and/or decrease the frequency of relapse caused by MDR-TB or XDR-TB, as well as treatment of latent TB.

The insights hereof also provide the advantage that TB vaccination with recombinant adenovirus vector that comprises nucleic acid encoding the Ag85A, Ag85B and TB10.4 antigens of Mtb, especially with the rAd35 vector as described herein, can be performed without stratification or testing of the presence of (active) TB, since no Koch's phenomenon was observed upon administration of the vaccine to patients having active TB, nor to patients having latent TB as assessed in a different clinical trial. Thus, also provided are methods for post-exposure prophylaxis of TB by administering to a subject a recombinant adenovirus vector that comprises nucleic acid encoding the Ag85A, Ag85B and TB10.4 antigens of Mtb. Such subjects may have been exposed but not yet have clinical signs of TB, or have undiagnosed TB, or alternatively may already have clinical signs of TB and thus have active TB. In certain embodiments, the subjects may have latent TB. The administration of the vaccine hereof may slow down or prevent the development or progression of the disease.

Also for latent TB, the immunotherapeutic vaccination hereof may be combined with drug therapy. Examples of standard drug therapy regimens for treating latent TB comprise administering isoniazid during nine months, or alternatively rifampin for four months. Also, these standard drug regimens can be shortened hereof, e.g., by at least one month, at least two months, at least three months, etc.

The invention is further explained in the following examples. The examples do not limit the invention in any way. They merely serve to clarify the invention.

EXAMPLES

Example 1

Clinical Trial with Ad35-Based TB Vaccine (Ad35.TB-S) in Human Subjects

A randomized, double-blinded, placebo-controlled clinical trial on human subjects was performed to evaluate the safety and immunogenicity of Ad35.TB-S (Havenga et al., 2006; Radošević et al., 2007; WO 2006/053871) in individuals with prior or current tuberculosis. This trial was conducted to ensure that the vaccine did not elicit severe adverse reactions, such as Koch's phenomenon, in subjects with previously unrecognized or active tuberculosis. By ensuring the safety of the vaccine in patients clinically documented to have tuberculosis, the vaccine could then be administered widely to larger populations in future studies without the need for extensive TB testing among subjects.

The study was designed as a dose escalation study where the vaccine dosage was increased in successive patient groups. Patients were enrolled sequentially, with the patients receiving the lowest dosage of vaccine enrolled and tested first. Conversely, patients receiving the highest vaccine dosage were enrolled last after the safety profile of the lower vaccine dosages had been ascertained. Enrollees were stratified based on time from the beginning of TB treatment. The "on-treatment" stratum consists of individuals who have active TB and who are currently undergoing treatment between one to four months prior to Study Day 0, Subjects in the "post-treatment" stratum had begun TB treatment at least 12 months prior to Study Day 0. The subjects were stratified as such since it was unclear whether individuals who suffered from active TB or cured of TB were at higher risk of developing Koch's phenomenon following vaccination containing TB antigens. Subjects from both the "on-treatment" and "post-treatment" strata were vaccinated once intramuscularly (IM) at Study Day 0 with 1 ml of $3\times10^8$ (Group 1) and $3\times10^9$ (Group 2) viral particles (vp). Subjects in Group 3 were vaccinated with two dosages of $3\times10^{10}$ vp at Study Day 0 and Study Day 42. Placebo controls were vaccinated in sterile buffer solution, which was identical to the buffer used to formulate the vaccine (20 mM Tris, 2 mM $MgCl_2$, 25 mM NaCl, sucrose 10% w/v, polysorbate-80 0.02% w/v). At the end of the study, thirty-one patients from the "on-treatment" and "post-treatment" groups each received Ad35.TBS. Thus, a total of sixty-two TB-infected patients received the Ad35.TB-S vaccine in this study and these patients were followed up over a period of six months.

To assess the safety of the vaccine in patients, investigators carried out serial injection site examinations, pulmonary function tests, chest radiography (CT scans), serum hematology, chemistry and monitored collection of solicited and unsolicited adverse events. Mild to moderate injection site reactions were more often observed after the first dose of injection in the "on-treatment" versus the "post-treatment" stratum. Nonetheless, frequency of unsolicited adverse events and differences in pulmonary function tests were not evident between dose groups or between strata. Importantly, at all vaccine dosages tested, Ad35.TB-S did not elicit any immunopathology similar to Koch's phenomenon, which indicates that the vaccine is safe to be used among adults with a history of pulmonary TB.

Immunogenicity of the vaccine was assessed by stimulation of cryopreserved peripheral blood mononuclear cells (PBMCs) collected at specific time points with peptide pools containing TB antigens Ag85A, Ag85B and TB10.4. Intracellular cytokine staining (ICS) and flow cytometry were subsequently carried out to identify whether the cytokines IL-2, IFN-γ and/or TNF-α were produced by CD4 and CD8 lymphocytes upon stimulation with the TB antigens described above. The results of the immunogenicity study for the "on-treatment" stratum are depicted in FIGS. 1 to 4.

Figure 2:
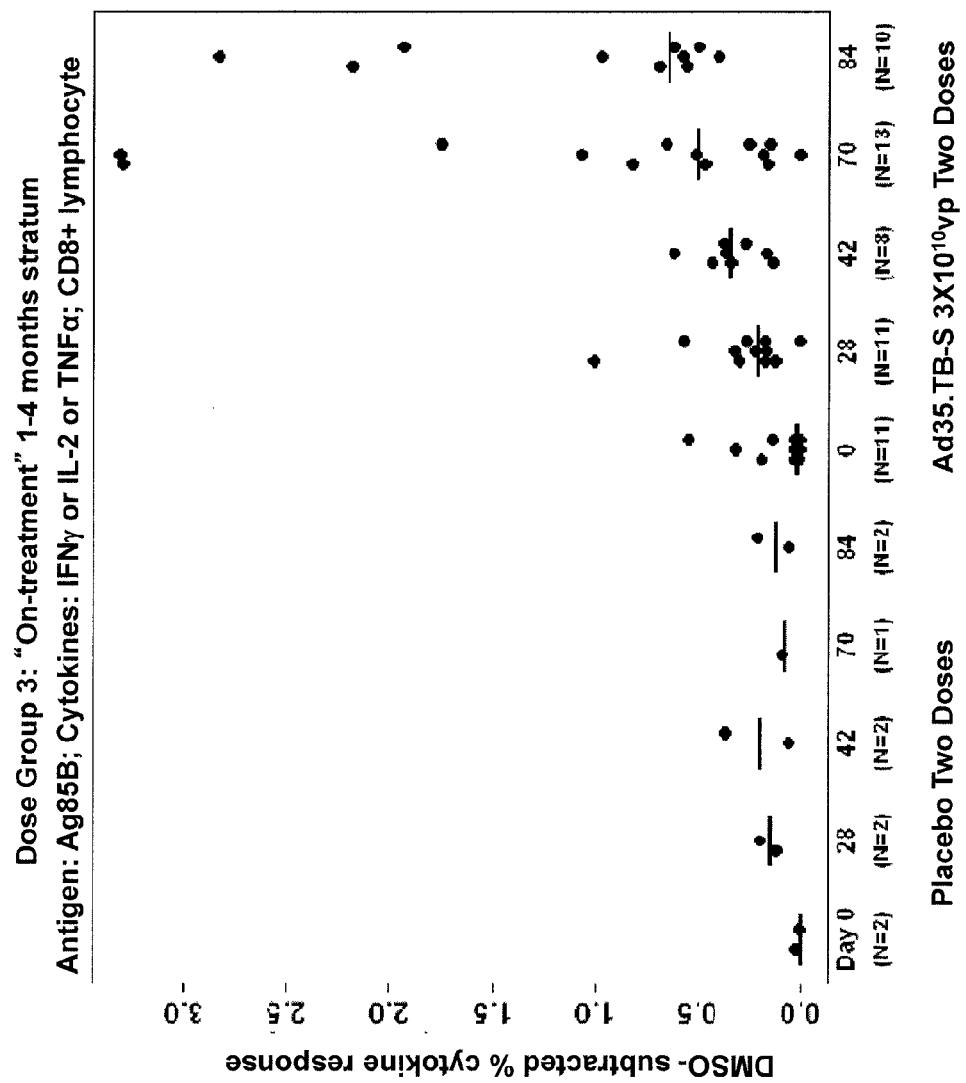
FIG. 2. Increase in the percentage of CD8 lymphocytes over time-releasing IFNγ or IL-2 or TNF-α upon stimulation with pooled peptides of Ag85B among vaccinees receiving $3\times10^{10}$ virus particles (vp) when compared to placebo control.
Figure 3:
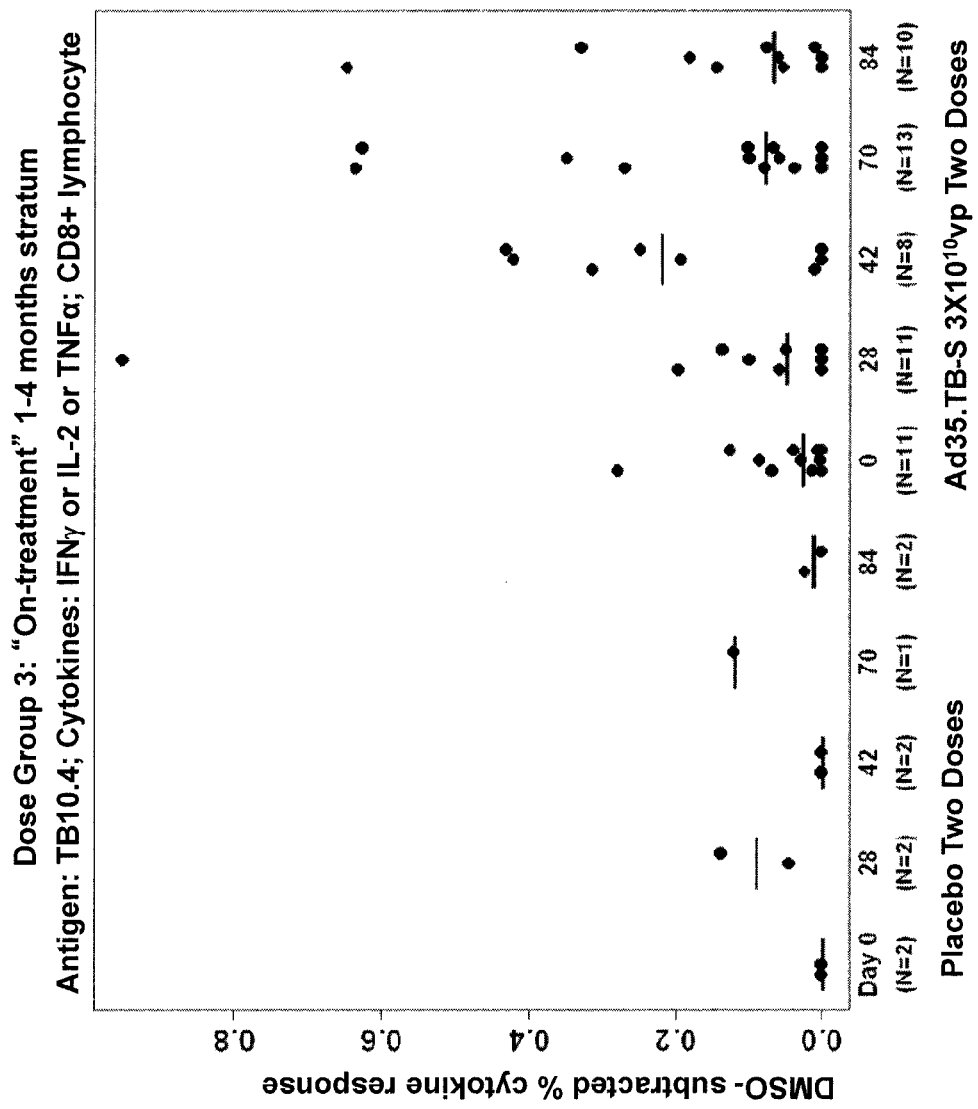
FIG. 3. Increase in the percentage of CD8 lymphocytes over time-releasing IFNγ or IL-2 or TNF-α upon stimulation with pooled peptides of TB10.4 among vaccinees receiving $3\times10^{10}$ virus particles (vp) when compared to placebo control.
Figure 4:
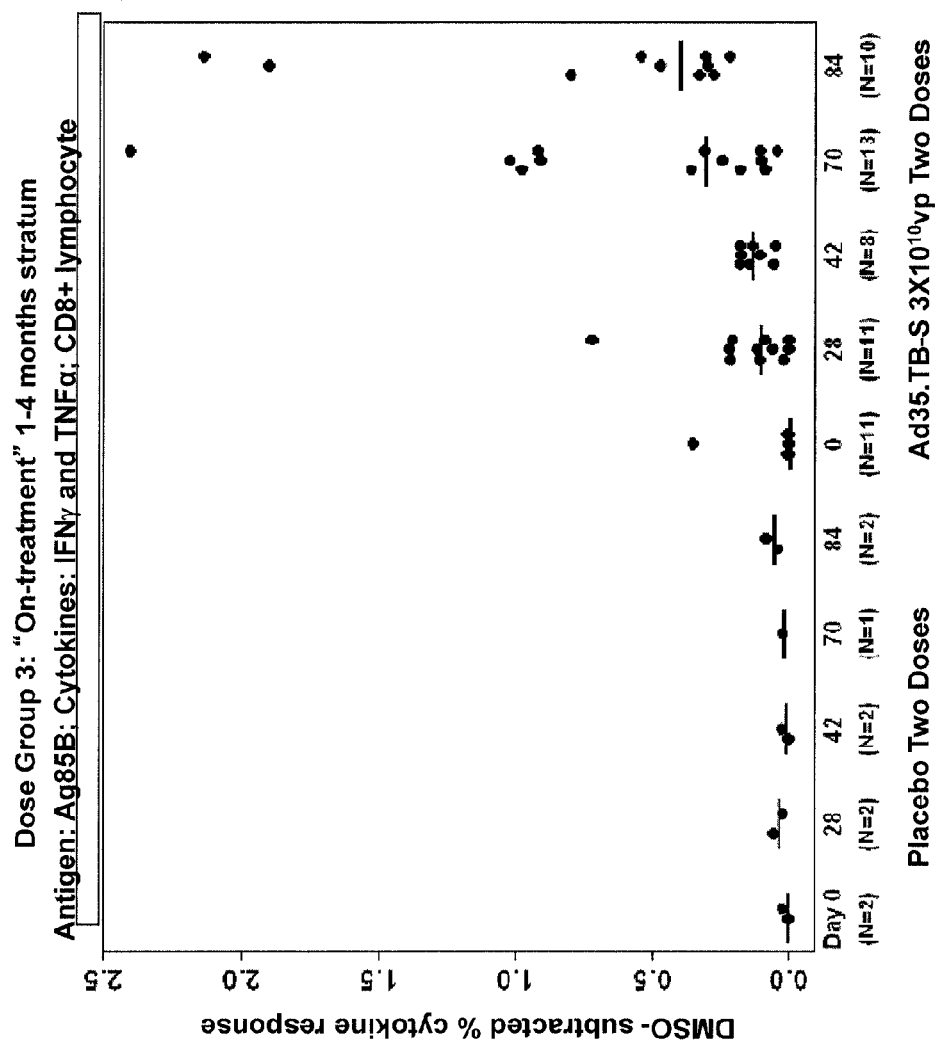
FIG. 4. Increase in the percentage of polyfunctional CD8 lymphocytes over time-releasing IFNγ and TNF-α upon stimulation with pooled peptides of Ag85B among vaccinees receiving $3\times10^{10}$ virus particles (vp) when compared to placebo control.

FIGS. 1 to 4 show the results of the ICS study carried out for subjects in the "on-treatment" stratum from Group 3 who were administered $3\times10^{10}$ vp of the vaccine at Study Day 0 and 42. The ICS measures the percentage of CD8 lymphocytes releasing IFNγ or TNFα or IL-2 upon stimulation with pooled peptides containing antigens 85A (FIG. 1), 85B (FIGS. 2 and 4) and TB 10.4 (FIG. 3). Measurements were taken at specific time points between Day 0 and Day 84 (FIGS. 1 to 4). Responses were found at all doses and appeared to be dosage-dependent, and to demonstrate a booster effect. For all three antigens tested, a higher percentage of CD8 lymphocyte cytokine responses were detected for the vaccinated group compared to placebo (FIGS. 1 to 4). These increased responses are particularly evident with Ag85B (FIG. 2). At later time points, some vaccinated subjects developed more than 1% of Ag85B-specific CD8 cells, which in some cases reached as high as 3% (FIG. 2). Polyfunctional T lymphocytes that secrete more than one cytokine are considered to be an important T cell subset in natural host immunity against TB disease. Intriguingly, vaccination with Ad35.TB-S resulted in an increased percentage of polyfunctional CD8 T lymphocytes expressing both IFNγ and TNFα (FIG. 4). Results of the ICS assay depicting the presence of CD8 cells expressing IFNγ and TNFα upon stimulation with Ag85B can be seen in FIG. 4, where the percentage of Ag85B-specific polyfunctional CD8 cells increased markedly following vaccination at Day 0 and Day 42 when compared to the placebo control group. It is of particular relevance to observe that CD8 lymphocytes from the placebo group, which originates from individuals infected with Mtb but did not receive vaccination with Ad35.TB-S, were less responsive to stimulation with antigens 85A, 85B or TB10.4 (FIGS. 1 to 4), pointing toward a clear lymphocyte tolerance against these Mtb antigens.

Taken together, the results of these immunological studies strongly indicate that the vaccine is immunogenic in Mtb-infected individuals who are normally unable to mount an immune response against Mtb antigens. This can be clearly observed by comparing the immune responses of the subjects in the placebo group to subjects who were vaccinated with Ad35.TB-S (FIGS. 1-4). The results of this trial suggests that the vaccine possesses an intrinsic ability to break the tolerance induced by the Mtb infection against host-induced immune responses, without resulting in immunopathological damage manifesting as Koch's phenomenon. This is the first trial of a novel recombinant TB vaccine conducted in individuals with a history of pulmonary TB that shows a good safety record with the ability to induce tolerance-breaking immune responses.

A separate clinical trial has demonstrated the safety and immunogenicity of the same vaccine in subjects with latent TB (data not shown), demonstrating that the vaccine can also be safely used (without induction of Koch's phenomenon) in such subjects, to induce immunogenic responses against at least one and preferably more of the antigens in the vaccine.

Example 2

Proof of Concept Study to Show the Treatment-Shortening Effect of the Ad35.TB-S Vaccine on Tuberculosis Drug Therapy in Mice Here, a method to show the TB chemotherapy-shortening effect of Ad35.TB-S is described. The method utilizes an established mouse model for TB drug chemotherapy, which is adapted for experimentation with the Ad35.TB-S vaccine.

Treatment of humans with Isoniazid, Rifampicin and Pyrazinamide in the first two months followed by Rifampicin and Isoniazid for the remaining four months of therapy results in a 1% to 2% chance of disease relapse (Neurmberger, 2008; Fox et al., 1999). In mice, similar therapy results in a 0% to 10% chance of relapse (Neurmberger, 2008). In a recent study, BALB/C mice exhibited a 0% relapse proportion when treated with this six-month standard regimen, which rose to 90% when treatment was shortened to four months (Williams et al., 2009). In that study, "relapse" was defined as isolation of 1 or greater CFU after plating the entire lung homogenate three months beyond completion of therapy (Williams et al., 2009).

Figure 5:
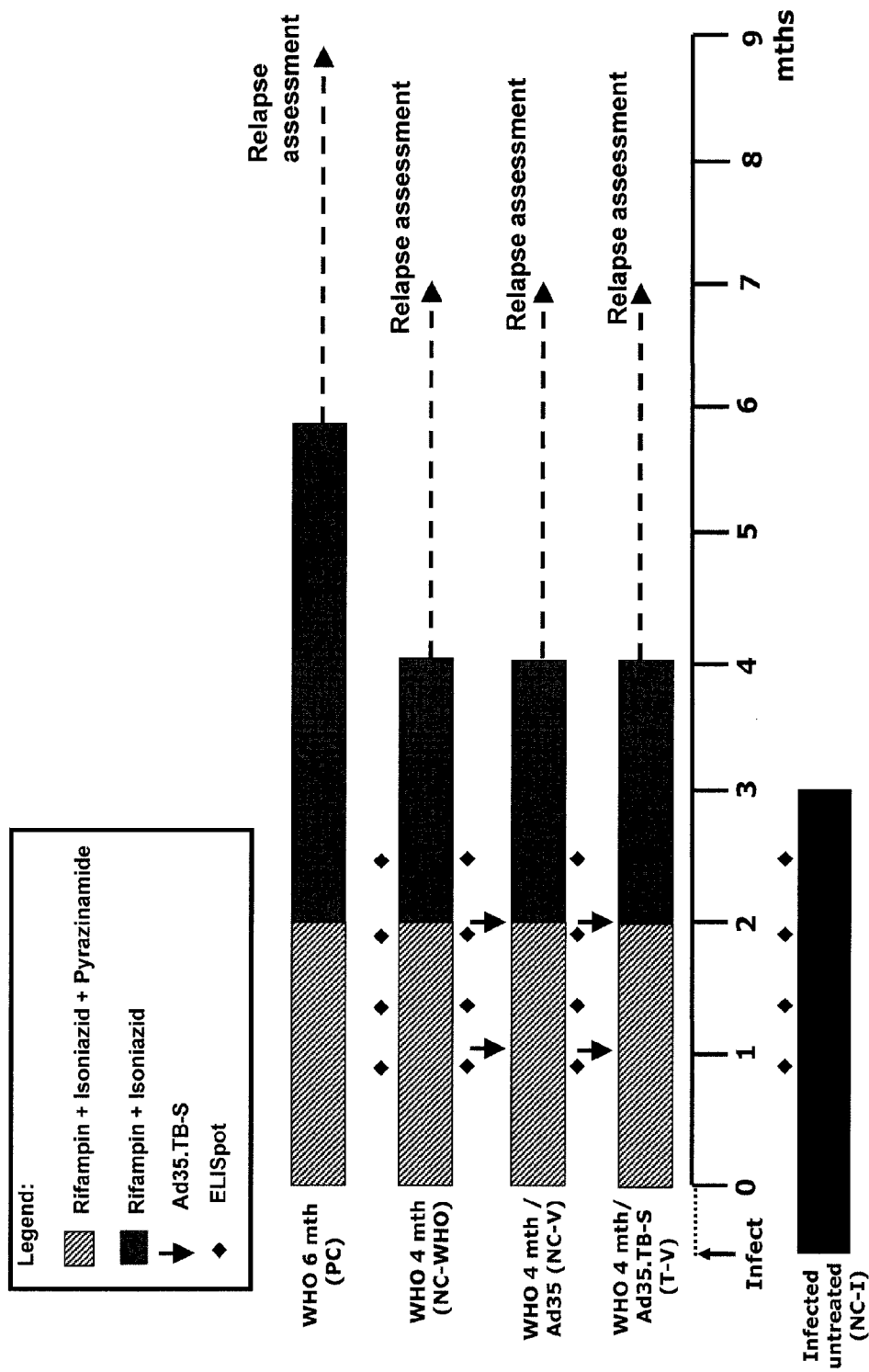
FIG. 5. Scheme of the animal study to demonstrate the chemotherapy-shortening effect of Ad35.TB-S with details on the timing of vaccination and immunological studies.

Based on the approach by Williams et al., the following experiment was designed to detect the ability of a recombinant adenovirus vector that comprises nucleic acid encoding the Ag85A, Ag85B and TB10.4 antigens of Mtb (here, Ad35.TB-S) to reduce the likelihood of relapse when therapy is shortened to a maximum of four months (FIG. 5). BALB/C mice were infected via the aerosol route with the Mtb strain $H_{37}Rv$ two weeks prior to allocation into five different groups. The first group served as positive control (PC) where animals were treated with the standard six-month WHO treatment regimen and have a known relapse occurrence of approximately 0%. The second group consisted of mice that were treated with the four-month WHO treatment regimen, that served as negative control (NC-WHO) and are known to relapse approximately 90% of the time. The third group comprised of animals that were infected with TB but not treated, and served as control for the Mtb infection (NC-I). The fourth group consisted of animals that were treated with the four-month WHO regimen, and vaccinated with Ad35 empty vector at months 1 and 2 of the treatment regimen (NC-V). The NC-V group served as negative control to monitor any vaccination-related adverse effects. In order to test the effect of Ad35.TB-S vaccination on prevention of relapse, a group of animals were treated with the four-month WHO regimen and vaccinated with Ad35.TB-S at one and two months following treatment initiation (T-V). The dosage of $10^{10}$ viral particles for the vaccine and empty vector control in this study was determined to be optimal based on immunogenicity in pilot studies. If vaccination with Ad35.TB-S results in a more efficient sterilizing activity after four months of TB chemotherapy than the standard chemotherapy alone, the proportion of vaccinated animals that relapse after treatment cessation is lower than the unvaccinated controls (T-V vs NC-WHO and NC-V).

At specific time points indicated in FIG. 5, ELISpot assays (K. Radosevic et al., 2007; M. Havenga et al., 2006; A. A. Lemckert et al., 2005) were conducted to determine T cell responses to the vaccine antigens. Specifically, splenocytes isolated from animals in each group were stimulated with antigens from *M. tuberculosis* encoded within the vaccine such as Ag85A, Ag85B and TB10.4. For Ag85A, known CD4 and CD8 peptides were used to enable characterization of the exact T cell subset stimulated in the study. The magnitude of IFN-gamma secretion upon stimulation with antigen was used as an indicator of T cell responsiveness. The results of the ELISpot study indicated that when compared to the control groups (NC-WHO and NC-V), the vaccine significantly boosted the immune responses against all antigens tested in the T-V group. For almost all antigens used, the immune responses induced by vaccination were significantly higher in the T-V group than the NC-I group, which contains a higher burden of bacteria systemically. There was also a consistently higher CD8 response to Ag85A noted within the vaccine T-V group. These promising immunogenicity results suggest that the vaccine, when utilized as an adjunct to TB chemotherapy in mice, was able to overcome T cell unresponsiveness that resulted from chronic TB infection.

To support the data obtained from the immunogenicity ELISpot studies and identify potential correlates of protection, multiplex cytokine analysis are conducted at each time point where the ELISpot analysis was carried out.

Histopathology was performed on lung samples obtained from animals in all groups to detect lung pathology that may be related to vaccination with Ad35.TB-S. For all experiments, samples from naïve mice served as baseline control. In all cases observed so far, no immunopathology was observed in the vaccinated T-V groups compared to the control groups.

These results confirm that the vaccine has an excellent safety profile to that seen in the human trials when used in the context of a TB infection in a closely controlled mouse model of infection.

It is expected that this experiment demonstrates that addition of vaccine to the chemotherapy regimen results in a decreased occurrence of relapse when compared to standard chemotherapy alone due to the enhanced immune responses elicited by the vaccine during therapy. Together, these results indicate that Ad35.TB-S can be used in conjunction with chemotherapy to shorten treatment duration and/or relapse rate and/or decrease in bacterial burden.

The length of treatment with antibiotics, the antibiotics used and the moment(s) of vaccination with the adenovirus vaccine are easily varied in this model. For example, the length of treatment with antibiotics is shortened to three months, two months, six weeks, four weeks, and shorter if deemed useful.

Example 3

The Effect of Therapeutic Vaccination by Heterologous Boosting of Ad35.TB-S with Ad26.TB-S Vaccines in a Mouse Model of TB Therapy The first heterologous prime-boost vaccine was trialed in humans by the group of Adrian Hill at Oxford (Schneider et al., 1998) in a trial designed to study the immunogenicity of a prophylactic vaccine against malaria. It was then observed that priming and boosting with different vectors carrying the same antigens resulted in a markedly enhanced immune response, which was due to the proliferation of memory T cells.

Figure 6:
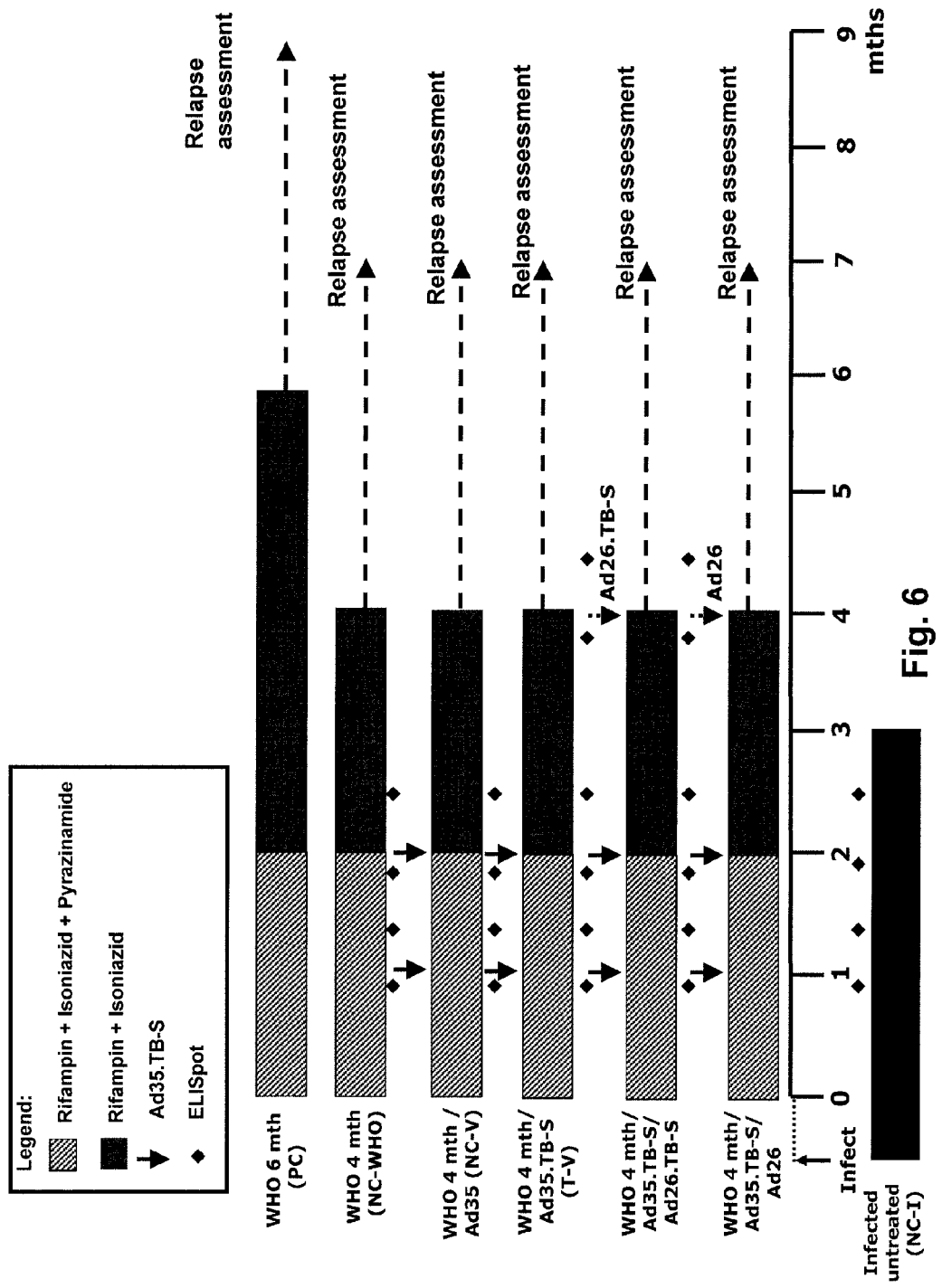
FIG. 6. Scheme of the animal study to demonstrate the chemotherapy-shortening effect by heterologous prime-boost with Ad35.TB-S followed by Ad26.TB-S with details on the timing of vaccination and immunological studies.

To test if priming with Ad35 and boosting with Ad26 would markedly result in enhanced immunogenicity as well as a decrease in relapse proportions upon shortening of TB therapy, two additional arms were added to the study shown in Example 2 (FIG. 6). In one arm, an additional vaccination of Ad26.TB-S containing the same antigens as the Ad35.TB-S was given at the end of the four-month therapy. Should the Ad26.TB-S boost enhance the immune response and target slow-growing intracellular persisters at this stage of the infection, the proportion of animals relapsing at the end of the study in this arm would be even lower than the group that received two vaccinations of Ad35.TB-S at one and two months of therapy. To control for the effect of Ad26 vector alone, another arm was added. This Ad26 control group is expected to relapse at the same proportion as the group that received two Ad35.TB-S vaccinations alone (T-V).

To determine if the Ad26.TB-S boost resulted in enhanced immunogenicity, ELISpot assays were conducted prior to immunization and two weeks after vaccination as indicated in FIG. 6. The results of the ELISpot study was highly encouraging as the Ad26.TB-S vaccination resulted in a significant boost to the T cell responses that exceeded the highest responses seen with the initial Ad35.TB-S vaccination during therapy. In contrast, the control vector did not elicit any boosting effect, confirming that the immune responses were targeted to the antigens contained in the vector.

As described in Example 2, histopathology samples are taken at each time point to ensure that no immunopathology develops as a result of boosting with Ad26.TB-S.

REFERENCES

Burke D. S. Of postulates and peccadilloes: Robert Koch and vaccine (tuberculin) therapy for tuberculosis. *Vaccine* 1993; 11(8):795-804.

Cardona P. J. RUTI: a new chance to shorten the treatment of latent tuberculosis infection. *Tuberculosis* (Edinb). 2006 May-July; 86(3-4):273-89.

Clinical trial of 6-month and 4-month regimens of chemotherapy in the treatment of pulmonary tuberculosis: the results up to 30 months. *Tubercle*. 1981; 62 (2):95-102.

Churchyard G. J., G. Kaplan, D. Fallows, R. S. Wallis, P. Onyebujoh, G. A. Rook. Advances in immunotherapy for tuberculosis treatment. *Clin. Chest Med.* 2009 December; 30(4):769-82.

Fan M., X. Chen, K. Wang, et al. Adjuvant effect of *Mycobacterium vaccae* vaccine on recurrent treated pulmonary tuberculosis: a meta-analysis. *Chinese Journal of Evidence-Based Medicine* 2007; 7 (6): 449-55.

Fox W., G. A. Ellard, and D. A. Mitchison. Studies on the treatment of tuberculosis undertaken by the British Medical Research Council tuberculosis units, 1946-1986, with relevant subsequent publications. *Int. J. Tuberc. Lung Dis.* 1999 October; 3(10 Suppl 2):S231-79.

Ha S. J., B. Y. Jeon, J. I. Youn, S. C. Kim et al. Protective effect of DNA vaccine during chemotherapy on reactivation and reinfection of *Mycobacterium tuberculosis*. *Gene Ther.* 2005 April; 12(7):634-8.

Havenga M., R. Vogels, D. Zuijdgeest, K. Radosevic, et al., 2006. Novel replication-incompetent adenoviral B-group vectors: high vector stability and yield in PER.C6® cells. *J. Gen. Virol.* 87:2135-2143.

Lemckert A. A., S. M. Sumida, L. Holterman, R. Vogels et al. Immunogenicity of heterologous prime-boost regimens involving recombinant adenovirus serotype 11 (Ad11) and Ad35 vaccine vectors in the presence of anti-Ad5 immunity. *J. Virol.* 2005 August; 79(15):9694-701.

Lowrie D. B., R. E. Tascon, V. L. Bonato, V. M. Lima, et al. Therapy of tuberculosis in mice by DNA vaccination. *Nature* 1999 Jul. 15; 400(6741):269-71.

Mitchison D A. 2005. The diagnosis and therapy of tuberculosis during the past 100 years. *Am. J. Respir. Crit. Care Med.* 171:699-706.

Nuermberger E. Using animal models to develop new treatments for tuberculosis. *Semin. Respir. Crit. Care Med.* 2008 October; 29(5):542-51.

O'Connor K. A., A. Holguin, M. K. Hansen, S. F. Maier, L. R. Watkins. A method for measuring cytokines from small samples. *Brain, Behaviour and Immunity* 2004, 18 (3); 274-280.

Radošević K., C. W. Wieland, A. Rodriguez, G. J. Weverling, et al. 2007. Protective immune responses to a recombinant adenovirus type 35 Tuberculosis vaccine in two mouse strains: CD4 and CD8 T-cell epitope mapping and role of gamma interferon. *Infect. Immunity* 75:4105-4115.

Schneider, J. et al. Enhanced immunogenicity for CD8+ T cell induction and complete protective efficacy of malaria DNA vaccination by boosting with modified vaccinia virus Ankara. *Nat. Med.* 4, 397-402 (1998).

Taylor J. L., O. C. Turner, R. J. Basaraba, J. T. Belisle, et al. 2003. Pulmonary necrosis resulting from DNA vaccination against Tuberculosis. *Infect. Immun.* 71:2192-2198.

Weichold F. F., S. Mueller, C. Kortsik, W. E. Hitzler, et al. 2007. Impact of MCH class alleles on the *M. tuberculosis* antigen-specific CD8+ T-cell response in patients with pulmonary tuberculosis. *Genes and Immunity* 8, 334-343.

Williams K. N., S. J. Brickner, C. K. Stover, T. Zhu et al. Addition of PNU-100480 to first-line drugs shortens the time needed to cure murine tuberculosis. *Am. J. Respir. Crit. Care Med.* 2009 Aug. 15; 180(4):37'-6.

Zhu D., S. Jiang, X. Luo. Therapeutic effects of Ag85B and MPT64 DNA vaccines in a murine model of *Mycobacterium tuberculosis* infection. *Vaccine* 2005 Aug. 31; 23(37): 4619-24.

The invention claimed is:

1. A method of treating a patient having active tuberculosis (TB), the method comprising:
    administering to the patient a recombinant adenovirus vector comprising nucleic acid encoding Ag85A, Ag85B, and TB10.4 antigens of *Mycobacterium tuberculosis*, and
    treating the patient further with drug therapy for tuberculosis, wherein the drug therapy comprises:
    administration of isoniazid, rifampin, pyrazinamide, and ethambutol to the patient.

2. A method of treating a patient having active tuberculosis (TB), the method comprising:
    administering to the patient a recombinant adenovirus vector comprising nucleic acid encoding Ag85A, Ag85B, and TB10.4 antigens of *Mycobacterium tuberculosis* (Mtb), and
    treating the patient further with drug therapy for tuberculosis, wherein the bacterial burden of Mtb as measured in a group of patients at a given time after the initiation of drug therapy is lower as compared to the burden at the same time point without the administration of said recombinant adenovirus vector.

3. The method according to claim 1, wherein the nucleic acid encodes Ag85A, Ag85B and TB10.4 antigens as a fusion protein.

4. The method according to claim 1, wherein the recombinant adenovirus vector is a replication-deficient human adenovirus of serotype 35.

5. A method of treating a patient having active tuberculosis, the method comprising:
    administering to the patient a recombinant adenovirus vector comprising nucleic acid encoding Ag85A, Ag85B, and TB10.4 antigens of *Mycobacterium tuberculosis*, wherein the recombinant adenovirus vector is a replication-deficient human adenovirus of serotype 26.

6. A method of treating a patient having active tuberculosis (TB), the method comprising:
    administering to the patient a recombinant adenovirus vector comprising nucleic acid encoding Ag85A, Ag85B, and TB10.4 antigens of *Mycobacterium tuberculosis* (Mtb), wherein the recombinant adenovirus vector is administered in a heterologous prime-boost regimen.

7. The method according to claim 6, wherein the heterologous prime-boost regimen comprises administration of vectors of a recombinant human adenovirus serotype 35 vector comprising nucleic acid encoding Ag85A, Ag85B and TB10.4 antigens of Mtb and of a recombinant human adenovirus serotype 26 vector comprising nucleic acid encoding Ag85A, Ag85B and TB10.4 antigens of Mtb.

8. A method of treating a patient having active tuberculosis (TB), the method comprising:
    administering to the patient a recombinant adenovirus vector comprising nucleic acid encoding Ag85A, Ag85B, and TB10.4 antigens of *Mycobacterium tuberculosis* (Mtb), wherein the TB is pulmonary TB.

9. A method of treating a patient having active tuberculosis (TB), the method comprising:
    administering to the patient a recombinant adenovirus vector comprising nucleic acid encoding Ag85A, Ag85B, and TB10.4 antigens of *Mycobacterium tuberculosis*

(Mtb), wherein the patient has an infection with multi-drug-resistant Mtb (MDR-TB) or extremely drug-resistant Mtb (XDR-TB).

10. A method of treating a patient having active tuberculosis, the method comprising:
administering to the patient a recombinant adenovirus vector comprising nucleic acid encoding Ag85A, Ag85B, and TB10.4 antigens of *Mycobacterium tuberculosis* (Mtb), wherein the recombinant adenovirus vector comprising nucleic acid encoding Ag85A, Ag85B, and TB10.4 antigens of Mtb is administered to the patient more than once.

* * * * *